United States Patent [19]

Horodysky et al.

[11] Patent Number: 4,532,057
[45] Date of Patent: Jul. 30, 1985

[54] LUBRICANT COMPOSITION COMPRISING THE REACTION PRODUCT OF A VICINAL DIOL AND A DIHYDROCARBYL PHOSPHITE

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 528,360

[22] Filed: Aug. 31, 1983

[51] Int. Cl.³ .............................................. C10M 1/45
[52] U.S. Cl. ................................. 252/49.8; 260/937; 260/953; 260/980
[58] Field of Search ............... 252/49.8; 260/921, 937, 260/953, 967, 980

[56] References Cited

U.S. PATENT DOCUMENTS

| | | | |
|---|---|---|---|
| 3,152,164 | 10/1964 | Oswald | 252/49.8 |
| 3,159,664 | 12/1964 | Bartlett | 252/49.8 |
| 4,005,159 | 1/1977 | Koch et al. | 252/49.8 |
| 4,312,767 | 1/1982 | Adams et al. | 252/49.8 |

Primary Examiner—Jacqueline V. Howard
Attorney, Agent, or Firm—Alexander J. McKillop; Michael G. Gilman; Van D. Harrison, Jr.

[57] ABSTRACT

Lubricants and liquid fuel composition containing a hydrogen phosphite-vicinal diol reaction product provide additional protection to metal parts in contact by reducing the amount of friction.

20 Claims, No Drawings

LUBRICANT COMPOSITION COMPRISING THE REACTION PRODUCT OF A VICINAL DIOL AND A DIHYDROCARBYL PHOSPHITE

BACKGROUND OF THE INVENTION

1. Field of the Invention

This invention relates to friction reducing additives for lubricants and liquid fuels. More particularly, the invention relates to lubricant and fuel compositions to which has been added a phosphorus-containing compound.

2. Discussion of the Prior Art

The metal surfaces of machinery or engines operate under heavy or normal loads wherein metal are under friction, even when being lubricated. Thus, there is always metal wear which can be excessive. It is clear that lubricants used to protect the metal surfaces do not completely prevent wear at the points of metal to metal contact. Consequently, the performance of the machine or engine will suffer, and in aggravated cases the machine or engine may become completely inoperative from the excessive wear caused by the friction.

There have been many attempts to devise additive systems to improve the friction properties of a lubricant. The non-metallic phosphonate derivatives of the present invention are believed to be capable of overcoming some of the deficiencies of prior art additives and to provide lubricating oil compositions with enhanced friction characteristics.

U.S. Pat. No. 2,758,971 describes a class of metal phosphonates which are disclosed as having properties which prevent breakdown of oils at high temperatures.

U.S. Pat. No. 2,792,374 discloses the alkali metal salts of certain alkyl alkylphosphonic acids as defoamants in aqueous systems.

U.S. Pat. No. 4,356,097 teaches an engine crankcase lubricating oil containing a dihydrocarbyl hydrocarbyl-phosphate, which oil exhibits reduced friction.

U.S. Pat. No. 2,982,727 discloses lubricating oil compositions containing certain salts of oxygen-containing esters of phosphorus. The esters are phosphonates similar to those described in U.S. Pat. No. 2,758,971.

However, no art is known that teaches or suggests the reaction product of the present compositions.

SUMMARY OF THE INVENTION

In accordance with the invention, there are provided products of reaction made by reacting a dihydrocarbyl phosphite with a vicinal diol and a lubricant or liquid fuel composition comprising a major proportion of a lubricant and an antifriction amount of said product of reaction.

DESCRIPTION OF SPECIFIC EMBODIMENTS

Because of the relatively complex nature of the reaction that occurs when phosphites and vicinal diols are interacted, no precise structure can be assigned to the product. Thus, the final product will be referred to herein, both in the specification and the claims, as the product of the specified reaction.

However, it is believed that the reaction products comprise at least some of the following compounds, when using the proper reactants:

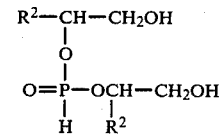

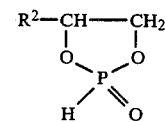

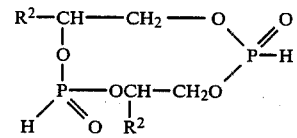

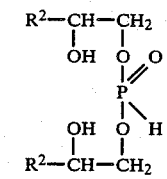

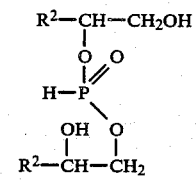

wherein $R^2$ is a hydrocarbyl group containing 8 to 28 carbon atoms, including mixtures thereof. $R^2$ can be linear, branched, saturated or unsaturated.

It will be understood that these are only illustrations and that numerous other compounds, as the art will understand, are possible. For brevity, these illustrations show the two hydroxyl groups on adjacent (vicinal) carbon atoms at the end of the chain.

The dihydrocarbyl phosphites used as reactants herein have the formula:

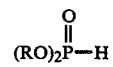

where R may be the same or different and is a hydrocarbyl group containing 1 to 6 carbon atoms. The phosphites include those wherein R in the formula is methyl, ethyl, propyl, butyl, pentyl, hexyl and the like. Methyl and ethyl are often preferred.

The hydrocarbyl vicinal diols contemplated for use in this invention are hydrocarbyl diols having vicinal hydroxyls. They have the formula:

wherein $R^1$ is a hydrocarbyl group containing 10 to 30 carbon atoms, including mixtures thereof. $R^1$ can be linear or branched, saturated or unsaturated. The two hydroxyl groups are preferably near the end of the hydrocarbyl chain and are on adjacent carbon atoms (vicinal).

Among the diols contemplated are 1,2-decanediol, 1,2-dodecanediol, 1,2-tetradecanediol, 1,2-pentadecanediol, 1,2-hexadecanediol, 1,2-heptadecanediol, 1,2-octadecanediol, etc. mixed 1,2-$C_{15}$-$C_{18}$ alkanediols, mixed 1,2-$C_{13}$-$C_{16}$ alkanediols, and mixtures of all such diols, including mixtures of similar diols.

The vicinal diols can be synthesized using several methods known to the art. One such method, described in an article in *J. Am. Chem. Soc.*, 68, 1504 (1946), involves the hydroxylation of 1-olefins with peracids. Vicinal diols can also be prepared by the peroxytrifluoroacetic acid method for the hydroxylation of olefins as described in *J. Am. Chem. Soc.*, 76, 3472 (1954). Similar procedures can be found in U.S. Pat. Nos. 2,411,762, 2,457,329 and 2,455,892. These are incorporated herein by reference.

The diols can also be prepared via catalytic epoxidation of an appropriate olefin, followed by hydrolysis.

As disclosed hereinabove, the preferred vicinal diols contain 10 to 30 carbon atoms. This range is preferred because diols having much less than 10 or 12 carbon atoms have significantly less friction reducing properties, while in those having more than 20 carbon atoms, solubility constraints become significant. More preferred are the $C_{14}$ to $C_{18}$ hydrocarbyl groups and mixtures of such hydrocarbyl groups in which solubility, frictional characteristics and other properties appear to be maximized.

Other additives, such as detergents, dispersants, antioxidants, antiwear agents, extreme pressure additives, pour depressants, antirust additives and the like may be present in the composition. These may include phenates, sulfonates, succinimides, zinc dithiophosphates, polymers, calcium and magnesium containing additives and the like.

The reactants are preferably used in equimolar quantities. That is, the reaction mixture should contain at least one mole each of phosphite, and vicinal diol. The reactants can also be used in a ratio of from 1:1 up to 1:3, i.e., phosphite to diol, or more preferably from 1:1.5 to 1:2. Thus, an excess of diol is often preferred to an excess of phosphite. The invention, however, contemplates products made by using ratios of respective reactants, i.e. phosphite, to diol, within the ratios of 1:1 to 1:6.

The temperature of reaction will depend upon the solvent used, since the reaction will generally be run at the temperature of reflux. The temperature is not believed to be critical and the reaction can be run over a wide range of from about 80° C. to about 225° C., preferably from about 80° C. to about 150° C. Examples of useful solvents are toluene, benzene, xylene, cyclohexane, ethanol and the like, although a solvent is not required. Where a solvent is used, it should be one in which the products are soluble and which can be relatively easily removed, although in some case a lubricating oil can be used as a solvent and diluent.

Times of reaction are not critical, but they will vary depending upon the size and complexity of the reactants. Under normal conditions, the reaction with the contemplated reactants can be completed in from about 1 hour to about 10 hours, preferably from about 2 hour to about 6 hours.

The compounds of the invention are used with lubricating oils or greases to the extent of from about 0.1% to about 10% by weight of the total composition, preferably from about 0.2% to about 2% and with fuels to the extent of from about 5 lbs. to about 250 lbs. per 1000 bbls. of fuel. Furthermore, other additives, such as detergents, antioxidants, antiwear agents and the like may be present. These can include phenates, sulfonates, polymeric succinimides, zinc dialkyl or aryl dithiophosphates, polymers, calcium and magnesium salts, polymeric viscosity index improving additives such as olefin copolymers, sulfurized olefins and the like.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexane, octene, decene, and dodecene, etc. These vicinal diol-derived phosphites are especially effective in synthetic oils formulated using mixtures of synthetic hydrocarbon olefin oligomers and lesser amounts of hydrocarbyl carboxylate ester fluids. The other synthetic oils, which can be used alone with the phosphorus compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di-and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salt and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include the liquid hydrocarbons, such as gasoline, fuel oil and diesel oil and the liquid alcohols such as methyl alcohol and ethyl alcohol. The fuels also include mixtures of alcohols as well as mixtures of alcohols and liquid hydrocarbons.

Having described the invention in general aspects, the following Examples are offered as specific illustrations. Parts are by weight.

EXAMPLE 1

1,2-Mixed Pentadecanediol-Octadecanediol Derived Hydrogen Phosphite (3:1)

Approximately 360 g of the 1,2-mixed pentadecanedioloctadecanediol (obtained from Viking Chemical Co. as Vikol 158 containing about 28% 1,2-pentadecanediol, about 28% 1,2-hexadecanediol, about 28% 1,2-heptadecanediol and about 16% 1,2-octadecanediol) were charged to a glass reactor equipped with heater, agitator, Dean-Stark tube with condenser and provision for blanketing the vapor space with nitrogen. The contents were heated to 70° C. to liquify and 55 g of dimethyl hydrogen phosphite were slowly added. The reaction mixture was heated to 110° C. and held for 2 hours, held at 120° C. for 1 hour, and held at 130° C. for 1 hour. During this reaction period, methanol distilled over and condensed into the trap. The crude product was vacuum stripped at 150° C. to remove volatile materials. 379 g of finished additive were produced. The product was an amber fluid which became waxy on cooling.

EXAMPLE 2

1,2-Mixed Pentadecanediol-Octadecanediol Derived Hydrogen Phosphite (2:1)

Approximately 480 g of the 1,2-mixed pentadecanedioloctadecanediol of Example 1 were charged to a reactor equipped as described in Example 1. The contents were warmed to almost 70° C. and 110 g of dimethyl hydrogen phosphite were slowly added. The reactor contents were heated at 110° C. for 2 hours, 120° C. for 1 hour, 130° C. for 1 hour, during which times methanol evolution was noted. The temperature was then raised to 150° C. and the product was vacuum stripped to remove volatiles. The product was an amber fluid which became waxy on cooling.

EXAMPLE 3

1,2-Mixed Pentadecanediol-Octadecanediol Derived Hydrogen Phosphite (1:1)

Approximately 234 g of the 1,2-mixed pentadecanediol-octadecanediol of Examples 1 and 2 were charged to a reactor equipped as generally described in Example 1. The contents were warmed to about 65° C. and 104 g of dimethyl hydrogen phosphite were slowly added. The reactor contents were heated to 120° C. for 2½ hours and 130° C. for 2½ hours, during which times methanol evolution was noted. The reactor contents were warmed to 165° C. during another 2 hour period and then vacuum stripped to remove volatiles. Approximately 276 g of an amber fluid, which became waxy on cooling, was recovered.

EXAMPLE 4

1,2-Dodecanediol Derived Hydrogen Phosphite (2:1)

Approximately 200 g of 1,2-dodecanediol (obtained as Vikol 12 from Viking Chemical Co.) were charged to a reactor equipped as generally described in Example 1. The contents were warmed to about 60° C. and 55 g of dimethyl hydrogen phosphite were added. The reaction mixture was heated at 110° C. for 2 hours, 120° C. for 1 hour and 130° C. for 1 hour. Methanol was observed forming and collecting in the trap during this period. The temperature was raised to 145° C. and the product was vacuum topped. Approximately 222 g of amber fluid was recovered which became waxy after cooling. The mixture was heated up to 160° C. until water evolution stopped over a period of 5 hours. Approximately 28 ml. water were collected. The solvent was removed by vacuum distillation at 160° C. and the product was filtered through diatomaceous earth.

EVALUATION OF PRODUCTS

The compound were evaluated as friction modifiers in accordance with the following test.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F, 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches.

The results obtained are shown in Tables 1 and 2. The data in the tables are reported as percent reduction in coefficient of friction at two speeds. The friction-reducing phosphorus additives were evaluated in a fully formulated 5W-30 synthetic lubricating oil (Table 1) or a mineral lubricating oil (Table 2), each comprising an additive package including anti-oxidant, metallic detergent and ashless dispersant.

TABLE 1

Friction Test Results Using Low Velocity Friction Apparatus

| | Additive Conc. in Base Fluid Weight % | % Reduction in Coefficient of Friction at 5 Ft/Min | % Reduction in Coefficient of Friction at 30 Ft/Min |
|---|---|---|---|
| Base Fluid (fully formulated synthetic oil based automotive engine oil containing detergent/dispersant/inhibitor performance package) SAE 5W30 | — | 0 | 0 |
| Example 1 Plus Base Fluid | 1 | 30 | 27 |
| Example 2 Plus Base Fluid | 1 | 25 | 22 |
| Example 3 Plus Base Fluid | 2 | 16 | 22 |

TABLE 2

Friction Test Results Using Low Velocity Friction Apparatus

| | Additive Conc. in Base Fluid Weight % | % Reduction in Coefficient of Friction at 5 Ft/Min | % Reduction in Coefficient of Friction at 30 Ft/Min |
|---|---|---|---|
| Base Fluid (fully formulated mineral oil based automotive engine oil containing detergent/dispersant/inhibitor performance package) SAE 10W40 | — | 0 | 0 |
| Example 1 Plus Base Fluid | 1 | 52 | 45 |
| Example 2 Plus Base Fluid | 1 | 35 | 28 |
| Example 3 Plus Base Fluid | 2 | 27 | 29 |
| Example 4 Plus Base Fluid | 1 | 32 | 25 |

We claim:

1. A product of reaction obtained by reacting a vicinal diol containing 10 to 30 carbon atoms with a dihydrocarbyl phosphite containing 1 to 6 carbon atoms, the reaction being carried out at from about 80° C. to about 225° C. using a mole ratio of diol to phosphite of from about 1:1 to about 3:1.

2. The product of claim 1 wherein the vicinal diol has the formula $$R^1(OH)_2$$

wherein $R^1$ is a hydrocarbyl group containing 10 to 30 carbon atoms.

3. The product of claim 2 wherein the diol is selected from the group consisting of 1,2-decanediol, 1,2-dodecanediol, 1,2-tetradecanediol, 1,2-pentadecanediol, 1,2-hexadecanediol, 1,2-hepteadecanediol, 1,2-octadecanediol and mixtures thereof.

4. The product of claim 3 wherein the diol is mixed 1,2-$C_{15}$ through $C_{18}$ alkanediols.

5. The product of claim 1 wherein the hydrocarbyl group is selected from the group consisting of methyl, ethyl, propyl, butyl, pentyl and hexyl.

6. The product of claim 1 wherein the diol is 1,2-mixed pentadecanediol-octadecanediol and the phosphite is dimethyl hydrogen phosphite.

7. The product of claim 1 wherein the diol is 1,2-dodecanediol and the phosphite is dimethyl hydrogen phosphite.

8. A lubricant composition comprising a major proportion of a lubricating oil or a grease therefrom and a friction reducing amount of a product of reaction obtained by reacting a vicinal diol containing 10 to 30 carbon atoms with a dihydrocarbyl phosphite containing 1 to 6 carbon atoms, the reaction being carried out at from about 80° C. to about 225° C. using a mole ratio of diol to phosphite of from about 1:1 to about 3:1.

9. The composition of claim 8 wherein the vicinal diol has the formula $$R^1(OH)_2$$

wherein $R^1$ is a hydrocarbyl group containing 10 to 30 carbon atoms.

10. The composition of claim 9 wherein the diol is selected from the group consisting of 1,2-decanediol, 1,2-dodecanediol, 1,2-tetradecanediol, 1,2-pentadecanediol, 1,2-hexadecanediol, 1,2-hepteadecanediol, 1,2-octadecanediol and mixtures thereof.

11. The composition of claim 10 wherein the diol is mixed 1,2-$C_{15}$ through $C_{18}$ alkanediols.

12. The composition of 8 wherein the hydrocarbyl group is selected from the group consisting of methyl, ethyl, propyl, butyl, pentyl and hexyl.

13. The composition of claim 8 wherein the diol is 1,2-mixed pentadecanediol-octadecanediol and the phosphite is dimethyl hydrogen phosphite.

14. The composition of claim 8 wherein the diol is 1,2-dodecanediol and the phosphite is dimethyl hydrogen phosphite.

15. The composition of claim 8 wherein the lubricant is selected from the group consisting of (1) a mineral oil, (2) a synthetic oil or a mixture of synthetic oils, (3) a mixture of (1) and (2) and (4) a grease of (1), (2) or (3).

16. The composition of claim 15 wherein the lubricant is a mineral oil as defined in (1).

17. The composition of claim 15 wherein the lubricant is a synthetic oil as defined in (2).

18. The composition of claim 15 wherein the lubricant is a mixture of oils defined by (1) and (2).

19. The composition of claim 15 wherein the lubricant is a grease from any of (1) to (3).

20. A method of reducing fuel consumption in an internal combustion engine which comprises (1) lubricating said engine with a composition comprising a major proportion of a lubricating oil and a fuel reducing amount of a product of reaction obtained by reacting a vicinal diol containing 10 to 30 carbon atoms with a dihydrocarbyl phosphite containing 1 to 6 carbon atoms the reaction being carried out at from about 80° C. to about 225° C. using a mole ratio of diol to phosphite of from 1:1 to about 3:1.

* * * * *